United States Patent [19]
Tang

[11] Patent Number: 4,618,621
[45] Date of Patent: Oct. 21, 1986

[54] METHOD FOR TREATING MEDICAL CONDITIONS INVOLVING CEREBRAL ISCHEMIA

[75] Inventor: Andrew H. Tang, Portage, Mich.

[73] Assignee: The Upjohn Company, Kalamazoo, Mich.

[21] Appl. No.: 653,385

[22] Filed: Sep. 21, 1984

[51] Int. Cl.⁴ .................. A61K 31/40; A61K 31/165; A61K 31/395
[52] U.S. Cl. .................. 514/408; 514/210; 514/617
[58] Field of Search .............. 424/324, 274; 514/210, 514/408, 617

[56] References Cited

U.S. PATENT DOCUMENTS 4,145,435  3/1979  Szmuszkovicz ............... 424/274
4,359,476  11/1982  Kaplan et al. ................. 424/274
4,360,531  11/1982  McMillan et al. ............. 424/274
4,438,130  3/1984  Kaplan ......................... 424/274

Primary Examiner—Stanley J. Friedman
Attorney, Agent, or Firm—John T. Reynolds

[57] ABSTRACT

A method for treating cerebral ischemia conditions by administering to the afflicted patient an effective amount of a compound of formula (I)

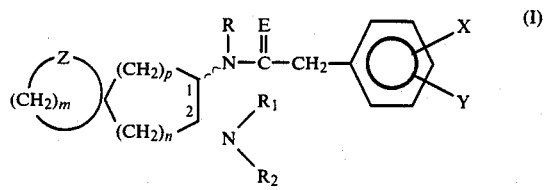

where p, m, R, $R_1$, $R_2$, E, X, Y and Z are as defined in the specification, e.g., $(5\alpha,7\alpha,8\beta)$-(−) or (±)-3,4-dichloro-N-methyl-N-[7-(1-pyrrolidinyl)-1-oxaspiro[4.5]dec-8-yl]benzeneacetamide, or

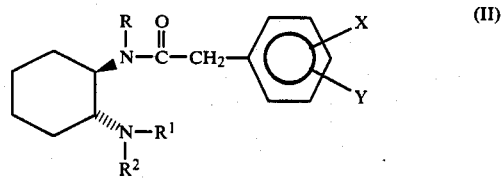

where R, $R_1$, $R_2$, X and Y are as defined in the specification, e.g., (−) or (±)-trans-2-(3,4-dichlorophenyl)-N-methyl-N-[2-(1-pyrrolidinyl)cyclohexyl]benzeneacetamide, or a pharmaceutically acceptable salt thereof.

4 Claims, No Drawings

METHOD FOR TREATING MEDICAL CONDITIONS INVOLVING CEREBRAL ISCHEMIA

INTRODUCTION

This invention relates to the use of certain N-(2-aminocyclohexyl)benzeneacetamide compounds as drugs to prevent the damaging consequences of ischemia (lack of blood flow) in the brain and spinal cord of warm-blooded animal patients. More particularly this invention provides a process or method for treating patients suffering from stroke, brain trauma, cardiovascular collapse and related conditions to prevent brain and/or spinal damage due to reduced blood flow.

BACKGROUND OF THE INVENTION

Cerebral ischemia, or lack of blood in the brain, results from a number of clinical conditions. For instance, stroke involves blockade of one or more of the arteries in the brain; head injuries obstruct blood flow to undamaged parts of the brain; cardiac arrest or circulatory shock deprive adequate blood supply to the brain and spinal cord; brain tumor could reduce passage of blood in cerebral vessels. The consequence of cerebral ischemia is most serious. Due to the great demand for oxygen and glucose by brain cells for warm-blooded animals, neurons lose their functions after seconds of complete ischemia. Damage becomes irreversible when ischemia is sustained for several minutes. Dependent on the area of the brain involved, death or long-term disability can be expected from cerebral ischemia.

Models for measuring cerebral ischemia in laboratory animals are used for the studies of the pathophysiology and experimental drug therapy. Occlusion of both common carotid arteries for sufficiently long periods of time produce death in the Mongolian gerbils and rats of the Fischer 344 strain. Similar carotid occlusion for five minutes under halothane anesthesia in the gerbils produce no death but a delayed cell loss in a specific area of the hippocampus of the brain. There was also a characteristic behavioral change in the post-ischemic gerbils marked by hyper-activity and perseveration in locomotion. Death, cell damage and behavioral and cognitive impairment from cerebral ischemia all have direct clinical parallel and have predictive value in evaluation of drug treatment.

The discovery that naloxone, a specific narcotic antagonist, had beneficial effects on circulatory shocks suggested to many investigators that the endogenous opiate systems may be involved in the pathophysiology of the cardiovascular system (review by Holaday, 1983). In the study of naloxone on spinal shock in cats, Faden et al. (1981) reported that naloxone produced a pressor response and improved spinal cord perfusion following spinal cord injury. In addition, the naloxone-treated cats had a smaller degree of long-term neurologic impairment compared to the saline-treated controls. The findings were confirmed by Young et al. (1981). A potential therapeutic use of naloxone in stroke was suggested by the study of Baskin et al. (1982) where baboons were rendered hemiplegic through selected occlusion of cerebral arteries. Naloxone treatment reduced the neurologic deficits, apparently independent of systemic circulatory effects. Subsequent studies with naloxone on the Mongolian gerbil models of cerebral ischemia led to discrepant findings. Whereas Hosobuchi et al. (1982) used unilateral carotid occlusion in the gerbils and found naxolone to reduce the post-ischemic neurologic deficit, Holaday and D'Amato (1982) failed to find any beneficial effect with naloxone using both unilateral and bilateral carotid occlusions. Both groups of investigators, however, did find morphine to exacerbate the post-stroke deficits. There is, at this time no specific and effective treatment for cerebral ischemia and cerebral edema resulting from the various causes. This invention provides a new course of treatment for this type of medical condition. References:

Baskin, D. S., Kieck, C. F. and Hosobuchi, Y.: *Life Science*, 31:2201, 1982.

Faden, A. L., Jacobs, T. P. and Holaday, J. W.: *Science*, 211:493, 1981.

Holaday, J. W.: *Biochemical Pharmacology*, 32:573, 1983.

Holaday, J. W. and D'Amato, R. J., *Life Science*, 31:385, 1982.

Hosobuchi, Y., Baskin, D. S. and Woo, S. K., *Science*, 215:69, 1982.

Young, W., Flamm, E. S., Demopoulos, H. G., Tomasula, J. H. and DeCrescito, V., *J. of Neurosurgery*, 55:209, 1981.

OBJECTIONS OF THE INVENTION

It is an object of this invention to provide the medical, including the veterinary, profession with some drug compounds which help alleviate the conditions or minimize the injurious consequences resulting from the lack of blood flow in the brain.

It is another object of the invention to provide a process for treating a warm-blooded animal patient, including humans, suffering from cerebral ischemia to relieve or alleviate or to minimize the consequences of temporary cereabral ischemia in such patient by administering to such patient an effective amount of a compound described hereinbelow to effect improvement in the patient's condition thereby.

SUMMARY OF THE INVENTION

Briefly, it has been discovered that certain N-(2-aminocyclohexyl)benzeneacetamide compounds of structures I and II hereinbelow reduce the adverse physiological consequences of temporary ischemia and this helps to prevent or minimize brain and/or spinal cord damage due to temporary reduced blood flow to the brain (cerebral ischemia). These compounds were originally discovered to be useful as analgesic compounds. We have further found that the more active enantiomers of these compounds are the trans-(−)stereo isomers of these compounds.

DETAILED DESCRIPTION OF THE INVENTION

More particularly, this invention provides a process for treating a warm-blooded animal patient suspected of presently suffering or suspected to be suffering from the effects of cerebral ischemia which comprises administering to such patient a safe, non-toxic effective amount of a compound selected from the group consisting of

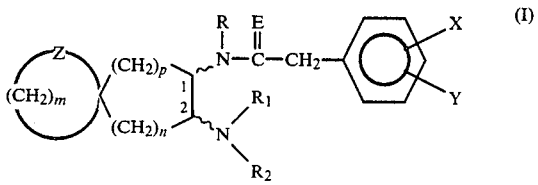

wherein p is a whole number integer 0, 1 or 2 and n is a whole number integer 1, 2 or 3, so that the resulting cycloaliphatic ring containing them has six carbon atoms;

m is 3 or 4;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-carboxyacylamino (—NHC(=O)$R_4$ where $R_4$ is hydrogen or $C_1$ to $C_2$-alkyl);

R is hydrogen or $C_1$ to $C_3$-alkyl;

$R_1$ and $R_2$, taken separately, are each hydrogen, $C_1$ to $C_3$-alkyl or allyl, $R_1$ and $R_2$, taken together with the nitrogen to which they are bonded, complete a ring selected from the group consisting of azetidinyl, pyrrolidinyl and piperidinyl, pyrrolyl, 3-pyrrolinyl, 3-azabicyclo[3.1.0-]hexan-3-yl and 3-azabicyclo[3.2.0]heptan-3-yl;

E is oxygen or sulfur;

Z is selected from the group consisting of oxygen, bivalent sulfur, and sulfinyl;

provided that the active Formula I compound contains an isomer thereof with an S absolute structural configuration at each of the one and two positions of the cyclohexane ring carbons bonded to the nitrogen atoms;

or a pharmacologically acceptable salt thereof; or

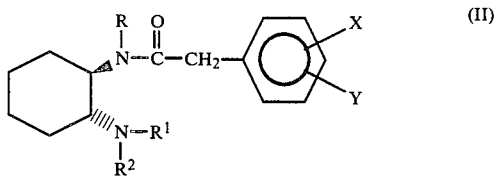

where R is hydrogen or methyl;

$R^1$ and $R^2$, taken separately, are hydrogen, $C_1$ to $C_3$-alkyl, or when $R^1$ is hydrogen or $C_1$ to $C_3$-alkyl, $R^2$ is allyl;

$R^1$ and $R^2$, taken together with the nitrogen to which they are bonded, complete a ring selected from the group consisting of azetidinyl and pyrrolidinyl;

X and Y are independently selected from the group consisting of hydrogen, a halogen having an atomic number of from 9 to 35, trifluoromethyl, $C_1$ to $C_3$-alkyl, methoxy, azido and phenyl, and at least one of X and Y is a substituent other than hydrogen, and when one of X and Y is azido, phenyl, methoxy or trifluoromethyl, the other of X and Y is hydrogen, and when R is hydrogen, both of X and Y are substituents other than hydrogen, which compounds of Formula II contain the compound having an (S,S) absolute configuration;

or a pharmaceutically acceptable salt thereof.

Methods known in the art for the determination of absolute configuration of chemical compounds, including the above compounds, are exemplified x-ray crystallography procedures, circular dichroism (CD) procedures, optical rotary dispersion (ORD) procedures, nuclear magnetic resonance (NMR) spectroscopy in a chiral environment, and the like.

Examples of acids suitable for making pharmaceutically acceptable acid addition salts of the above compounds of Formulas I or II above for use according to this invention include such acids as hydrogen chloride, hydrogen bromide, hydrogen iodide, sulfuric acid, orthophosphoric acid, acetic acid, lactic acid, citric acid, succinic acid, benzoic acid, salicyclic acid, pamoic acid, cylohexanesulfonic acid, methanesulfonic acid, 1- and 2-naphthalene sulfonic acids, p-toluenesulfonic acid, maleic acid, fumaric acid, succinic acid and the like.

Dosage ranges for use of these compounds can vary from about 0.001 to about 25 mg./kg. of the patient's body weight depending upon the compound being used. A general daily range of from about 0.1 to about 350 mg. in single or divided dosage unit forms given two to four times a day for an adult animal is suggested. A single adult human dose ranging from about 0.1 to about 1000 mg. per day can be used depending upon the condition being treated, the age and weight of the patient, the compound being used, and similar factors.

The term "dosage form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals.

Since the patients being treated for the possible cerebral ischemia according to this invention are usually those who have been hurt badly in some physical accident or incident, or who are in need of prompt medical attention because of some internal medical problem, e.g., stroke, etc., it is contemplated that the first dosages of these drug compounds will be given by injection or by intravenous administration methods. However, after the patient is conscious and responding to an attending physician, the physician may prefer to administer subsequent dosages of these drug compounds to the patient by the oral route. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diulents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.1 to about 350 mg. of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain brain protection effects within the aforesaid effective non-toxic range. Preferred dosages for most applications are 0.05 to 2.0 mg./kg. of body weight.

The useful pharmaceutical dosage unit forms of these compounds in pharmaceutical formulations are preferably adapted for systemic administration to obtain removal of the effects of ischemia comprising an effective, non-toxic amount of a compound according to Formula I or II, or as its pharmacologically acceptable salt.

Examples of compounds of Formula I above which can be used in this invention include:

1. trans-3,4-dichloro-N-methyl-N-[8-(1-pyrrolidinyl)-1,4-dioxaspiro[4.5]dec-7-yl]benzeneacetamide,
2. trans-3,4-dichloro-N-methyl-N-[7-(1-pyrrolidinyl)-1,4-dioxaspiro[4.5]dec-8-yl]benzeneacetamide,
3. trans-3,4-dichloro-N-methyl-N-[7-(1-pyrrolidinyl)-1,4-dioxaspiro-[4.5]dec-6-yl]benzeneacetamide,
4. trans-4-bromo-N-methyl-N-[7-(1-pyrrolidinyl)-1,4-dioxaspiro[4.5]dec-8-yl]benzamide,
5. $(5\alpha,7\alpha,8\beta)$-3,4-dichloro-N-methyl-N-[7-(1-pyrrolidinyl)-1-oxa-spiro[4.5]dec-8-yl]benzeneacetamide and its levo isomer (6),
6. $(5\alpha,7\alpha,8\beta)$-(−)-3,4-dichloro-N-methyl-N-[7-(1-pyrrolidinyl)-1-oxaspiro[4.5]dec-8-yl]benzeneacetamide, and
7. $(5\xi,6\alpha,7\beta)$-3,4-dichloro-N-[7-(dimethylamino)-1-oxaspiro[4.5]dec-6-yl]-N-methylbenzeneacetamide, and the like, or a pharmaceutically acceptable salt thereof.

Examples of compounds of Formula II which can be used according to this invention include:

trans-N-[2-(1-pyrrolidinyl)cyclohexyl]-N-methyl-2-(3,4-dichlorophenyl)acetamide, trans-N-[2-(1-pyrrolidinyl)cyclohexyl]-N-methyl-2-(3,4-dichlorophenyl)propionamide, trans-N-[2-(3-hydroxy-1-pyrrolidinyl)cyclohexyl]-N-methyl-2-(3,4-dichlorophenyl)acetamide, trans-N-[2-(1-azetidinyl)cyclohexyl]-N-methyl-2,(3,4-dichlorophenyl)acetamide, and the like, in their (S,S) absolute stereo configuration, or a pharmacologically acceptable salt thereof.

Compounds of the above Formula I are described and procedures for making them are disclosed in U.S. Pat. Nos. 4,360,531 and 4,359,476 and in U.S. Pat. No. 4,438,130.

Compounds of the above Formula II are described and procedures for making them are disclosed in U.S. Pat. Nos. 4,145,435 and 4,436,013.

Of these various compounds a lead compound of structure I being selected for advanced studies of the cerebral ischemia consequence control property (as well as its analgesic activity) is $(5\alpha,7\alpha,8\beta)(\pm)$-3,4-dichloro-N-methyl-N-[7-(1-pyrrolidinyl)-1-oxaspiro[4.5]dec-8-yl]benzeneacetamide which, as can be seen from the name, is mixed dextro (+) and levo (−) isomer form of the compound. We now know, however, that for the protection from cerebral ischemia alone (without considering the analgesic property) the levo (−) isomer of this compound, namely $(5\alpha,7\alpha,8\beta)$-(−)3,4-dichloro-N-methyl-N-[7-(1-pyrrolidinyl)-1-oxaspiro[4.5]dec-8-yl]benzeneacetamide is the more potent compound.

A lead compound of the structure II type for the use of this invention is the trans-2-(3,4-dichlorophenyl)-N-methyl-N-[2-(1-pyrrolidinyl)cyclohexyl]acetamide maleate (U-50,488E). This compound (A) as its (±) enantiomorphic mixture has the desired properties for treating the consequences of cerebral ischemia. More specific tests using the separate enantiomorph compound, illustrated by Example 2 hereinbelow, indicate that the active compound for the new use of this invention is the levo (−) isomer of the above compound, that is, trans(−)-2-(3,4-dichlorophenyl)-N-methyl-N-[2-(1-pyrrolidinyl)cyclohexyl]acetamide (U-53,444) as one of its pharmaceutically acceptable salts, such as the hydrochloride, the maleate or methanesulfonic acid salts.

The determination of the usefulness of the compounds included herein for their ability to eliminate or minimize the consequences of cerebral ischemic can be done in standard laboratory animal tests described in detailed Examples 1 and 2 hereinbelow, without intending that these Examples be limiting upon the scope of the invention.

EXAMPLE 1

EFFECT OF U-50,488 AGAINST CEREBRAL ISCHEMIA

Objectives

The purpose of this study was to evaluate the protective effects of U-50,488E against cerebral ischemia. We chose bilateral carotid occlusion (BCO) as the experimental model of cerebral ischemia in the Mongolian gerbil and the Fischer 344 strain of rats. The Mongolian gerbils are uniquely sensitive to BCO because of the absence of communication between the carotid and vertebral arterial supply to the brain. BCO for a duration beyond 10 minutes resulted in death for the majority of animals. We found that a shorter duration of five minutes of BCO under 2% halothane anesthesia produced no death. The post-ischemic gerbils were, however, hyperactive when placed in a novel environment and exhibited perseveration in their exploratory behaviors. Histological examination of the dorsal hippocampus of gerbils subjected to five-minute BCO revealed swelling of the pyramidal cells in the CA1 subfield 24 hours after the global ischemia. The same neurons were lost to degeneration when examined seven days after BCO. The behavorial and histological changes after five-minute BCO in the gerbils provided specific endpoints to evaluate the consequence of ischemic brain damage. As an extension of the above model of cerebral ischemia, we used a more prolonged period of BCO in gerbils and in rats, measuring lethality within one week post-ischemia. The lethal effects from BCO in Fischer 344 rats were used earlier in this laboratory to study ischemia-protective effects of drugs.

Methods and Materials

Subjects and Surgical Procedure

Male Mongolian gerbils weighing between 38–55 grams and female Fischer 344 rats weighing between 160–180 grams were used in this study. Bilateral carotid occlusion was carried out under anesthesia by 2% halothane in a mixture of 95% $O_2$ and 5% $CO_2$. Both common carotid arteries were occluded with microaneurysm clips for 5 or 10 minutes in the gerbil. The skin incision was closed with wound-clips and the animals were allowed to recover from anesthesia. For the rats, two procedures of BCO were used. In the first procedure, both common carotid arteries were ligated and cut under brief anesthesia. In the second procedure, the left common carotid artery was ligated permanently and the right common carotid artery was occluded with an aneurysm clip under brief halothane anesthesia. The animal was then placed in a holding box for four hours, at the end of which the clip was removed from the right cartoid artery under brief anesthesia. Survivors from BCO were housed in their home cage (suspended wire-mesh cages) and the length of survival was recorded for one week.

Behavorial Evaluation

Gerbils subjected to five-minute BCO were evaluated for spontaneous locomotor activities in a symmetrical Y-maze 24 hours after the surgical procedure. The experimental session was one hour in duration and measurements were (a) total number of arm entries, and (b) percentage of arm-entries which were not a return to the arm most recently occupied. The latter value represented the probability of "spontaneous alternation" in the exploratory locomotion.

Drug Evaluation

For the five-minute BCO procedure in gerbils, the test drugs were injected IP thirty minutes before the surgical operation. For the ten-minute BCO procedure in gerbils and four-hour BCO in rats, the drugs were injected IP thirty minutes before and again three hours after the operation. Groups of eight animals were treated with the same dose of a drug and compared to a control group which underwent the same operation but received no drug.

RESULTS

Spontaneous Locomotor Activity

Pretreatment with U-50,488E before five-minute (BCO) in the gerbil resulted in significant protection from the behavorial consequences of cerebral ischemia. At 30 mg./kg., the behavioral hyperactivity, measured by number of arm entry and spontaneous alternation, were both reversed (Table 1). No improvement was found with ethylketocyclazocine (EKC) at 1 and 3 mg./kg. Simultaneous administration of naloxone (MERCK INDEX, Tenth Edit., item 6208, p. 912) partially antagonized the effects of U-50, 488E on hypermotility (Table 2). The higher dose (3 mg./kg.) of naloxone as well as 10 mg./kg. of morphine also produced significant protection against the hypermotility from cerebral ischemia, although the effect was less complete than after U-50,488E. Table 3 shows that U-50,488E protected gerbils from the ischemic behavorial changes, not only when injected before but also when injected immediately after the carotid occlusion.

Lethal Ischemia

U-50,488E (30 mg./kg.) protected against delayed death in Mongolian gerbils receiving ten-minute BCO (Table 4). Despite the protective effects of U-50,488E in ten-minute occlusion, no significant effect was found with fifteen-minute occlusions.

Fischer 344 rats subjected to GCO developed neurological abnormality within the first few hours. When one of the carotid arteries was re-opened after four hours of occlusion, most of the animals died within a short time (less than one hour). Pretreatment with U-50,488E at 30 mg./kg. reduced the neurological signs during BCO and increased significantly the number of survivors (Table 5). EKC was found to be ineffective. In the procedure where both common carotid arteries were permanently ligated, U-50,488E delayed the lethal effect which was significant on the first day only.

Conclusion

Using the bilateral carotid occlusion models for cerebral ischemia in Mongolian gerbils and rats, significant protection was found with pretreatments of U-50,488E. The therapeutic potential of U-50,488E against stroke and other CNS trauma is suggested by the data from these tests.

TABLE 1

Effects of treatments on the post-ischemic hyperactivity and perseveration in Mongolian gerbils. The common carotid arteries were occluded for five minutes and locomotor activity was measured 24 hours later in the Y-maze for one hour. Drugs were administered intraperitoneally (IP), 30 minutes before the ischemic operation.

| Treatment | N | Dose Mg./Kg. | Maze Test Number of Arm Entries | Maze Test; % Spontaneous Alternations |
|---|---|---|---|---|
| Experiment I: | | | | |
| Ischemic, No drug | 7 | — | 904 ± 127 | 44.6 ± 2.9 |
| Ischemic, U-50,488E | 7 | 3 | 559 ± 68* | 43.0 ± 3.8 |
| Ischemic, U-50,488E | 8 | 10 | 712 ± 122 | 47.5 ± 1.8 |
| Ischemic, U-50,488E | 8 | 30 | 388 ± 66** | 54.4 ± 1.4** |
| Sham operated, No drug (norm) | 8 | — | 157 ± 21** | 58.5 ± 2.0** |
| Experiment II: | | | | |
| Ischemic, No drug | 8 | — | 1187 ± 106 | 40.6 ± 5.0 |
| Ethylketo-cyclazocine (EKC) | 8 | 1 | 934 ± 108 | 40.6 ± 3.1 |
| Ethylketo-cyclazocine | 8 | 3 | 963 ± 142 | 47.0 ± 3.0 |
| Sham operated, | 8 | — | 141 ± 22** | 58.9 ± 2.1** |

TABLE 1-continued

Effects of treatments on the post-ischemic hyperactivity and perseveration in Mongolian gerbils. The common carotid arteries were occluded for five minutes and locomotor activity was measured 24 hours later in the Y-maze for one hour. Drugs were administered intraperitoneally (IP), 30 minutes before the ischemic operation.

| Treatment | N | Dose Mg./Kg. | Maze Test Number of Arm Entries | Maze Test; % Spontaneous Alternations |
|---|---|---|---|---|
| No drug (norm) | | | | |

*— $P < 0.05$ comparing to No ischemic drug group.
**— $P < 0.01$ comparing to No drug ischemic group.

| Treatment | N | Dose Mg./kg. | Maze Test; Number of Arm Entries |
|---|---|---|---|
| Ischemic, No drug | 8 | — | 1038 ± 49 |
| Ischemic, U-50,488E | 8 | 30 | 297 ± 93$^{aa}$ |
| U-50,488E + Naloxone | 6 | 30 + 1 | 488 ± 105$^{aa}$ |
| U-50,488E + Naloxone | 8 | 30 + 3 | 602 ± 126$^{aa,b}$ |
| Naloxone | 7 | 3 | 765 ± 123$^{a,bb}$ |
| Morphone SO$_4$ | 7 | 10 | 608 ± 59$^{aa,b}$ |

$^{aa}P < 0.01$ comparing to No drug group
$^{a}P < 0.05$ comparing to No drug group
$^{bb}P < 0.01$ comparing to U-50,488E group alone
$^{b}P < 0.05$ comparing to U-50,488E group alone

TABLE 3

Protection from the post-ischemic hyperactivity in Mongolian gerbils. The carotid arteries were occluded for five minutes and activity was measured 24 hours later in the Y-maze test for one hour. U-50,488E was injected intraperitoneally (IP) either 30 minutes before or immediately after occlusion.

| Treatment | N | Dose Mg./kg. | Maze Test; Number of Arm Entries |
|---|---|---|---|
| Ischemic, No drug | 8 | — | 1187 ± 106 |
| U-50,488E before occlusion | 8 | 30 | 528 ± 74** |
| U-50,488E after occlusion | 8 | 30 | 768 ± 62** |

**$P < 0.01$ comparing to No drug group.

TABLE 4

Number of survivors per day in each treatment group after bilateral carotid occlusion in Mongolian gerbils. Under 2% fluothane anethesia, gerbils were occluded for (a) ten minutes or (b) fifteen minutes. Vehicle or drug was administered intraperitoneally (IP) thirty minutes before and three hours after the cerebral ischemia.

| Treatment | Dose Mg./Kg. | 1 | 2 | 3 | 4 | 5 | 6 | 7 |
|---|---|---|---|---|---|---|---|---|
| (a) 10 min. occlusion | | | | | | | | |
| Vehicle | — | 7/8 | 7/8 | 5/8 | 2/8 | 1/8 | 1/8 | 1/8 |
| U-50,488E | 30 | 7/8 | 7/8 | 6/8 | 6/8 | 6/8 | 6/8 | 6/8 |
| Fisher's P Value | | | | | 0.04 | 0.04 | 0.04 | |
| (b) 15 min. occlusion | | | | | | | | |
| Vehicle | — | 5/8 | 3/8 | 3/8 | 1/8 | 0/8 | 0/8 | 0/8 |
| U-50,488E | 30 | 4/8 | 3/8 | 2/8 | 2/8 | 1/9 | 1/9 | 2/9 |

TABLE 5

Number of survivors per day in each treatment group in Fischer 344 rates subjected to cerebral ischemia. Under 2% fluothane anesthesia: (a) the left carotid artery was permanently ligated and the right artery was clamped for four hours. Vehicle or drug was injected intraperitoneally (IP) thirty minutes before and two hours after occlusion. (b) Both carotid arteries were ligated and cut. Vehicle or U-50,488E was injected IP immediately and four hours after ligation.

| Treatment | Dose Mg./Kg. | 1 | 2 | 3 | 4 | 5 | 6 |
|---|---|---|---|---|---|---|---|
| (a) | | | | | | | |
| Vehicle | — | 3/8 | 3/8 | 3/8 | 3/8 | 3/8 | 3/8 |
| U-50,488E | 30 | 8/8 | 8/9 | 8/8 | 8/8 | 8/8 | 8/8 |
| Fisher's P Value | | 0.025 | .025 | .025 | .025 | .025 | .025 |
| Vehicle | — | 1/8 | 0/8 | 2/8 | 2/8 | 2/8 | 2/8 |
| Ethylketocyclazocine | 3 | 2/8 | 0/8 | 2/8 | 2/8 | 2/8 | 2/8 |
| (b) | | | | | | | |
| Vehicle | — | 2/10 | 1/10 | 1/10 | 1/10 | 1/10 | 1/10 |
| U-50,488E | 30 | 8/10 | 5/10 | 4/10 | 4/10 | 4/10 | 4/10 |
| Fisher's P Value | | 0.025 | NS | NS | NS | NS | NS |

Note:
NS means non-significant

EXAMPLE 2

ILLUSTRATION OF STEREO-SPECIFIC EFFECT OF U-50,488E IN PREVENTING CONSEQUENCES OF ISCHEMIA

U-50,488E is a specific opioid kappa receptor agonist with analgesic, diuretic and CNS depressant properties. It was found according to this invention also to protect against the consequences of cerebral ischemia and CNS trauma. The possibility that this brain protective effect is mediated through the kappa opioid receptors is the subject of this investigation.

Materials and Methods

The procedure of bilateral carotid occlusion in Mongolian gerbils to produce behavioral hyperactivity was described in Example 1 hereinabove, with the duration of occlusion changed from five to seven minutes. A group of animals with no drug treatment was always included as the parallel controls for comparison. In the survival study with gerbils, the duration of carotid occlusion was also changed from 10 to 15 minutes. The change was necessary due to an apparent increase in resistance to this manipulation in recent months. The procedure for carotid occlusion in the Fischer 344 rats was unchanged from the Example 1 procedure.

Results

The effects of drug pretreatment on ischemic survival are summarized in Table 1. In both gerbils and Fischer rats, the number of survivors at the end of one week was significantly increased in the group treated with U-53,444E[1] but not in the group treated with the same dose of U-53,445E[2].

[1] U-53,444E is trans(−)2-(3,4-dichlorophenyl)-N-methyl-N-[2-(1-pyrrolidinyl)cyclohexyl]acetamide maleate salt
[2] U-53,445E is the trans (+) enantiomer of the same compound The enantiomers of U-50,488E and two other kappa agonists were tested in the gerbil hyperactivity model by one injection 30 minutes before carotid occlusion (Table 2). Both enantiomers reduced the hyperactivity of the animals with the levo-isomer U-53,444E being more effective than U-53,444E. Neither EKC nor bremazocine reduced the hyperactivity although the change in spontaneous alternation was significantly reversed by the two kappa agonists. Since both EKC and bremazocine are fairly short-acting, the issue was investigated with the drug given by three injections, three hours apart, covering a longer time after cerebral ischemia. Table 3 shows that U-50,488E, EKC and bremazocine were all very effective in preventing the development of hyperactivity in the post-ischemic gerbils. The loss of spontaneous alternation was also significantly reversed by all three drugs. Using the same treatment protocol, the diuretic furosemide had no anti-ischemic effect.

Gerbils sacrificed 24 hours after seven-minute carotid occlusion exhibited cellular change in the pyrimidal neurons of the CA1 subfield in the dorsal hypocampus. The main feature was a swelling of the cell body. No difference was found between the control ischemic group and gerbils treated with three injections of U-50,488E at 3 or 30 mg./kg. Gerbils sacrificed on the eighth day post-carotid occlusion had extensive cell loss in the same area where cell swelling was found in the 24-hour post-ischemic group. The four gerbils treated with three injections of U-50,488E at 30 mg./kg. and sacrificed on the eighth day post-ischemia had only a mild degree of cell loss. The 3 mg./kg. group was not different from the control ischemic animals.

CONCLUSIONS

This invention detailed a novel method in medical treatment for treating patients afflicted with cerebral ischemia and the damaging consequences of the same. It was demonstrated in laboratory experiments that these classes of pharmacological agents known to pharmacologists as "kappa opiate agonists" and represented by the key chemical compound, U-50,488E, protects warm-blooded animals from lethal effects of prolonged cerebral ischemia. The behavioral and cognitive abnormality resulting from brief cerebral ischemia in gerbils were also protected by the pretreatment with U-50,488. The cellular damage and degeneration from the cerebral ischemia was minimized. The effective agent in the racemic mixture of U-50,488 was shown to be the (—) levo enantiomer. Although one single injection of U-50,488 before the ischemic attack was effective, injection after the ischemia was also beneficial and the best regimen of therapy being three injections before and after the beginning of ischemia. U-50,488 was further shown to be superior to two other "kappa opiate agonists" and a diuretic agent, furosemide in cerebral protection.

TABLE 6

Number of survivors per group after bilateral coratid occlusion in Fischer 344 rats and gerbils. Saline or drug was injected, intraperitoneally (IP), thirty minutes before and two hours after occlusion.

| Animals | Treatment | Dose (mg./kg.) | 24 Hr. | One Week |
|---|---|---|---|---|
| Gerbils | Saline | — | 5/8 | 2/8 |
| | U-53,444E | 30 | 7/8 | 7/8 (p = 0.04)* |
| | U-53,445E | 30 | 1/8 | 0/8 |
| Rats | Saline | — | 8/14 | 6/14 |
| | U-53,444E | 30 | 9/9 | 8/9 (p = 0.04) |
| | U-53,445E | 30 | 4/9 | 3/9 |

TABLE 6-continued

*Compared to the saline group

TABLE 7

Drug-effects on the development of hyper-activity in gerbils subjected to seven minutes of bilateral carotid occlusion. Spontaneous locomotor activities were measured in the automated Y-maze 24 hours after carotid occlusion. Drug treatment was by one injection 30 minutes before carotid occlusion.

| Experiments | Treatment | Dose | N++ | No. Arm-Entries/Hr | % Spontaneous Altern. |
|---|---|---|---|---|---|
| 1 | No Drug | — | 9 | 942 ± 127 | 50.1 ± 2.9 |
| | (Norm) Sham Operated | — | 8 | 118 ± 15** | 57.7 ± 2.3 |
| | U-53,444E | 30 mg./kg. | 9 | 381 ± 115** | 51.2 ± 2.0 |
| | U-53,445E | 30 mg./kg. | 9 | 555 ± 79* | 53.1 ± 2.0 |
| 2 | No Drug | — | 8 | 1242 ± 43 | 36.4 ± 1.5 |
| | (Norm) Sham Operated | — | 8 | 141 ± 18** | 61.5 ± 1.5** |
| | EKC | 0.1 mg./kg. | 8 | 1231 ± 198 | 44.6 ± 2.9* |
| | EKC | 0.3 mg./kg. | 7 | 1013 ± 198 | 47.1 ± 5.0* |
| | EKC | 1.0 mg./kg. | 8 | 934 ± 108 | 40.6 ± 3.1 |
| | EKC | 3.0 mg./kg. | 8 | 963 ± 142 | 47.0 ± 3.0 |
| 3 | No Drug | — | 15 | 1042 ± 116 | 39.3 ± 1.9 |
| | (Norm) Sham Operated | — | 8 | 173 ± 12** | 59.0 ± 1.9** |
| | Bremazocine | 0.1 mg./kg. | 8 | 924 ± 133 | 48.1 ± 1.5** |
| | Bremazocine | 0.3 mg./kg. | 8 | 626 ± 101* | 48.3 ± 2.7** |
| | Bremazocine | 1.0 mg./kg. | 8 | 956 ± 95 | 46.1 ± 1.7* |
| | Bremazocine | 3.0 mg./kg. | 8 | 732 ± 151 | 47.4 ± 2.2* |

**$P < 0.01$;
*$P < 0.05$; Student's t-test, comparing to the first group in each experiment
+ = N is the number of animals in the test group

TABLE 8

Protection against the development of hyperactivity and loss of spontaneous alternation in gerbil after seven minutes of bilateral carotid occlusion. Drugs were administered by three injections 30 minutes before carotid occlusion and at three hour intervals.

| Experiment | Treatment | Dose (mg./kg.) | N | No. Arm Entry/Hour | % Spontaneous Alternation |
|---|---|---|---|---|---|
| 1 | Vehicle | — | 8 | 1150 + −148 | 46.4 + −2.9 |
| | (Norm) Sham operated | — | 7 | 134 + −16** | 55.0 + −1.0* |
| | U-50,488E | 30 | 8 | 201 + −31** | 52.9 + −2.9* |
| | U-50,488E | 3 | 8 | 815 + −122 | 49.5 + −1.0 |
| 2 | Vehicle | — | 8 | 1262 + −81 | 36.5 + −3.5 |
| | (Norm) Sham | — | 8 | 109 + | 59.6 + −6.1** |

TABLE 8-continued

Protection against the development of hyperactivity
and loss of spontaneous alternation in gerbil after
seven minutes of bilateral carotid occlusion.
Drugs were administered by three injections 30 minutes before carotid
occlusion and at three hour intervals.

| Experiment | Treatment | Dose (mg./kg.) | N | No. Arm Entry/ Hour | % Spontaneous Alternation |
|---|---|---|---|---|---|
| | operated | | | 14** | |
| | Ethylketocyclazocine | 10 | 8 | 388 + −5** | 55.7 + −4.5** |
| | Ethylketocyclazocine | 1 | 8 | 702 + −3** | 48.6 + −3.0** |
| 3 | Vehicle | — | 8 | 946 + −140 | 46.1 + −2.7 |
| | (Norm) Sham operated | — | 6 | 137 + −16** | 63.0 + −3.2** |
| | Bremazocine | 10 | 8 | 257 + −64** | 52.6 + −2.0 |
| | Bremazocine | 1 | 8 | 419 + −78** | 53.1 + −1.7* |
| 4 | Vehicle | — | 10 | 910 + −70 | 44.9 + −2.8 |
| | (Norm) Sham operated | — | 6 | 144 + −17** | 60.0 + −0.8** |
| | Furosemide | 30 | 8 | 762 + −150 | 43.0 + −4.1 |
| | Furosemide | 3 | 8 | 1150 + −147 | 40.2 + −2.3 |

**$P < 0.01$;

*$P < 0.05$, Student's t-test, comparing to the first treatment group in each experiment.

I claim:

1. A process for treating a warm-blooded animal patient suffering from cerebral ischemia which comprises administering to such a patient a safe, non-toxic amount sufficient to prevent or to relieve the consequences of cerebral ischemia of a compound of the formula

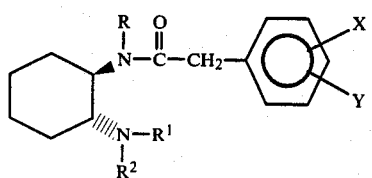

where
R is hydrogen or methyl;
$R^1$ and $R^2$, taken separately, are hydrogen, $C_1$ to $C_3$-alkyl, or when $R^1$ is hydrogen or $C_1$ to $C_3$-alkyl, $R^2$ is allyl;
$R^1$ and $R^2$, taken together with the nitrogen to which they are bonded, complete a ring selected from the group consisting of azetidinyl and pyrrolidinyl;
X and Y are independently selected from the group consisting of hydrogen, a halogen having an atomic number of from 9 to 35, trifluoromethyl, $C_1$ to $C_3$-alkyl, methoxy, azido and phenyl, and at least one of X and Y is a substituent other than hydrogen, and when one of X and Y is azido, phenyl, methoxy or trifluoromethyl, the other of X and Y is hydrogen, and when R is hydrogen, both X and Y are substituents other than hydrogen,
which compounds of Formula II contain the compound having an (S,S) absolute configuration; or a pharmaceutically acceptable salt thereof.

2. A process according to claim 1 wherein the active compound is one of Formula II in which the compound is in the trans-configuration,
R is methyl;
$R_1$ and $R_2$ are taken together with the nitrogen to which they are bonded to complete a pyrrolidine ring; and
X and Y are chloro in the 3- and 4-positions, or a pharmaceutically acceptable salt thereof.

3. A process according to claim 2 wherein the active compound is trans-N-[2-(1-pyrrolidinyl)cyclohexyl]-N-methyl-2-(3,4-dichlorophenyl)acetamide, or a pharmaceutically acceptable salt thereof.

4. A process according to claim 2 wherein the active compound is trans-(−)-2-(3,4-dichlorophenyl)-N-methyl-N-[2-(1-pyrrolidinyl)cyclohexyl]acetamide, or a pharmaceutically acceptable salt thereof.

* * * * *